USO11446044B2

(12) United States Patent
Bonnette et al.

(10) Patent No.: US 11,446,044 B2
(45) Date of Patent: *Sep. 20, 2022

(54) INFUSION CATHETER (71) Applicant: BOSTON SCIENTIFIC SCIMED, INC., Maple Grove, MN (US)

(72) Inventors: Michael J. Bonnette, Minneapolis, MN (US); Jason T. Anderson, Deephaven, MN (US); David B. Morris, Anoka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 251 days.

This patent is subject to a terminal disclaimer.

(21) Appl. No.: 16/721,518

(22) Filed: Dec. 19, 2019

(65) Prior Publication Data

US 2020/0138459 A1 May 7, 2020

Related U.S. Application Data (62) Division of application No. 15/617,562, filed on Jun. 8, 2017, now Pat. No. 10,543,006.

(Continued)

(51) Int. Cl.
*A61B 17/22* (2006.01)
*A61B 17/3203* (2006.01)
(Continued)

(52) U.S. Cl.
CPC ........ *A61B 17/22* (2013.01); *A61B 17/32037* (2013.01); *A61M 5/142* (2013.01);
(Continued)

(58) Field of Classification Search
CPC .......... A61M 25/0012; A61M 25/0015; A61M 25/0043; A61M 25/0054; A61M 25/0068;
(Continued)

(56) References Cited

U.S. PATENT DOCUMENTS 4,681,570 A * 7/1987 Dalton ................. A61M 1/285
604/523
4,738,667 A 4/1988 Galloway
(Continued)

FOREIGN PATENT DOCUMENTS

CN 203280485 U 11/2013
EP 0635242 B1 6/1999
(Continued)

OTHER PUBLICATIONS

International Search Report and Written Opinion dated Sep. 25, 2017 for International Application No. PCT/US2017/036562.

*Primary Examiner* — Nilay J Shah
(74) *Attorney, Agent, or Firm* — Seager, Tufte & Wickhem, LLP (57) ABSTRACT An infusion catheter system may deliver a therapeutic agent to a desired location in the body. The system may include an elongate catheter shaft having a proximal end region, a distal end region, a distal opening, and a lumen extending between the proximal end region and distal opening. The distal end region may include a coiled portion having a preformed coiled configuration including a plurality of helically wound rings. A plurality of apertures may be formed through a sidewall of the coiled portion. A guidewire may be configured to be slidably disposed within the lumen of the catheter shaft. The guidewire may include a proximal end region having a first cross-sectional dimension, an enlarged distal end region having a second cross sectional dimension greater than the first cross-sectional dimension, and an intermediate region disposed between the proximal end region and the distal end region.

17 Claims, 5 Drawing Sheets

Related U.S. Application Data (60) Provisional application No. 62/347,942, filed on Jun. 9, 2016.

(51) Int. Cl.
*A61M 25/09* (2006.01)
*A61M 5/142* (2006.01)
*A61M 5/178* (2006.01)
*A61M 25/00* (2006.01)
*A61B 17/221* (2006.01)

(52) U.S. Cl.
CPC .......... *A61M 5/178* (2013.01); *A61M 25/007* (2013.01); *A61M 25/0052* (2013.01); *A61M 25/0054* (2013.01); *A61M 25/09* (2013.01); *A61B 2017/2217* (2013.01); *A61B 2017/22038* (2013.01); *A61B 2017/22084* (2013.01); *A61M 25/0015* (2013.01); *A61M 2025/0057* (2013.01); *A61M 2025/0063* (2013.01); *A61M 2025/0915* (2013.01); *A61M 2205/0266* (2013.01)

(58) Field of Classification Search
CPC ............ A61M 25/007; A61M 25/0074; A61M 25/0138; A61M 25/09; A61M 2025/0079; A61M 2025/0163; A61M 2025/0063; A61M 2025/09058; A61M 2025/09133; A61M 2025/09141; A61B 2017/22038; A61B 17/32037; A61B 17/22
See application file for complete search history.

(56) References Cited

U.S. PATENT DOCUMENTS

| | | |
|---|---|---|
| 5,025,799 A | 6/1991 | Wilson |
| 5,122,136 A | 6/1992 | Guglielmi et al. |
| 5,250,034 A | 10/1993 | Appling et al. |
| 5,279,546 A | 1/1994 | Mische et al. |
| 5,554,114 A * | 9/1996 | Wallace .................. A61B 17/22 604/508 |
| 5,624,396 A | 4/1997 | McNamara et al. |
| 5,626,564 A | 5/1997 | Zhan et al. |
| 5,709,874 A * | 1/1998 | Hanson ..................... A61F 2/06 424/423 |
| 5,782,797 A | 7/1998 | Schweich, Jr. et al. |
| 5,800,408 A | 9/1998 | Strauss et al. |
| 5,873,865 A | 2/1999 | Horzewski et al. |
| 5,951,517 A | 9/1999 | Lampropoulos et al. |
| 5,957,901 A * | 9/1999 | Mottola ............... A61M 25/007 604/264 |
| 5,968,017 A | 10/1999 | Lampropoulos et al. |
| 5,997,487 A | 12/1999 | Kolehmainen et al. |
| 6,007,514 A * | 12/1999 | Nita .................. A61B 17/22012 604/22 |
| 6,027,487 A | 2/2000 | Crocker |
| 6,059,759 A | 5/2000 | Mottola et al. |
| 6,063,069 A | 5/2000 | Cragg et al. |
| 6,074,378 A * | 6/2000 | Mouri ............... A61M 25/0068 604/264 |
| 6,113,576 A | 9/2000 | Dance et al. |
| 6,179,813 B1 | 1/2001 | Ballow et al. |
| 6,179,828 B1 | 1/2001 | Mottola et al. |
| 6,391,018 B1 * | 5/2002 | Tanaka .............. A61M 25/0041 604/164.13 |
| 6,478,778 B1 | 11/2002 | Jacobsen et al. |
| 6,520,930 B2 | 2/2003 | Critchlow et al. |
| 6,524,300 B2 | 2/2003 | Meglin |
| 6,602,241 B2 | 8/2003 | Makower et al. |
| 6,652,536 B2 | 11/2003 | Mathews et al. |
| 6,676,637 B1 | 1/2004 | Bonnette et al. |
| 6,716,190 B1 | 4/2004 | Glines et al. |
| 6,755,813 B2 | 6/2004 | Ouriel et al. |
| 6,852,097 B1 | 2/2005 | Fulton, III |
| 6,936,025 B1 | 8/2005 | Evans et al. |
| 6,945,951 B1 | 9/2005 | Bonnette et al. |
| 7,163,533 B2 | 1/2007 | Hobbs et al. |
| 7,276,043 B2 | 10/2007 | Heath et al. |
| 7,399,307 B2 | 7/2008 | Evans et al. |
| 7,641,645 B2 | 1/2010 | Schur |
| 7,666,169 B2 | 2/2010 | Cowan et al. |
| 7,824,704 B2 | 11/2010 | Anderson et al. |
| 8,608,703 B2 | 12/2013 | Riles et al. |
| 8,702,678 B2 | 4/2014 | Comerota et al. |
| 8,840,637 B2 | 9/2014 | Fineberg |
| 8,858,497 B2 | 10/2014 | Di Palma et al. |
| 8,956,352 B2 | 2/2015 | Mauch et al. |
| 8,986,241 B2 | 3/2015 | Evans et al. |
| 8,998,843 B2 | 4/2015 | Bonnette et al. |
| 8,998,894 B2 | 4/2015 | Mauch et al. |
| 8,998,946 B2 | 4/2015 | Morero |
| 9,108,019 B2 | 8/2015 | Bonnette et al. |
| 2005/0080448 A1 | 4/2005 | Kear et al. |
| 2006/0064011 A1 | 3/2006 | Hong |
| 2006/0129091 A1 | 6/2006 | Bonnette et al. |
| 2006/0135870 A1 | 6/2006 | Webler |
| 2007/0203475 A1 * | 8/2007 | Fischer, Jr. .......... A61B 17/221 604/530 |
| 2007/0249964 A1 * | 10/2007 | Richardson ............ A61L 31/10 600/585 |
| 2008/0275393 A1 | 11/2008 | Bonnette et al. |
| 2009/0264770 A1 * | 10/2009 | Liu .................. A61B 17/22012 600/466 |
| 2010/0145356 A1 | 6/2010 | Fischer, Jr. et al. |
| 2010/0191175 A1 | 7/2010 | Couvillon, Jr. |
| 2011/0130756 A1 | 6/2011 | Everson et al. |
| 2011/0295305 A1 | 12/2011 | Morero |
| 2013/0046282 A1 | 2/2013 | O'Day et al. |
| 2014/0066915 A1 | 3/2014 | Zhou et al. |
| 2014/0336594 A1 | 11/2014 | Tano et al. |

FOREIGN PATENT DOCUMENTS

| | | |
|---|---|---|
| EP | 2762188 A1 | 8/2014 |
| GB | 2399017 A | 9/2004 |
| WO | 9613295 A1 | 5/1996 |
| WO | 0154754 A1 | 8/2001 |
| WO | 03043685 A2 | 5/2003 |
| WO | 2006034492 A1 | 3/2006 |
| WO | 2007092506 A2 | 8/2007 |
| WO | 2007092506 A3 | 12/2007 |

* cited by examiner

INFUSION CATHETER

CROSS-REFERENCE TO RELATED APPLICATIONS

This application is a divisional of U.S. patent application Ser. No. 15/617,562, filed Jun. 8, 2017, which claims the benefit of priority under 35 U.S.C. § 119(e) to U.S. Provisional Application No. 62/347,942, filed Jun. 9, 2016, the entire disclosure of which are herein incorporated by reference.

TECHNICAL FIELD

The disclosure is directed to accessory devices for use with catheters. More particularly, the disclosure is directed to devices to aid in removing or accelerating the removal of clots.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices.

In a first example, an infusion catheter system may comprise an elongate catheter shaft having a proximal end region, a distal end region, a distal opening, and a lumen extending between the proximal end region and distal opening. The distal end region of the elongate catheter shaft may include a coiled portion having a preformed coiled configuration including a plurality of helically wound rings. A plurality of apertures may be formed through a sidewall of the coiled portion and in fluid communication with the lumen of the catheter shaft. A guidewire may be configured to be slidably disposed within the lumen of the catheter shaft. The guidewire may include a proximal end region having a first outer diameter, a distal end region having a second outer diameter, the second outer diameter greater than the first outer diameter, and an intermediate region disposed between the proximal end region and the distal end region. The intermediate region may have a first flexibility greater than a second flexibility of the proximal end region.

Alternatively or additionally to any of the examples above, in another example, the coiled portion may be formed at least in part of a shape memory material.

Alternatively or additionally to any of the examples above, in another example, the distal end region of the guidewire may be configured to be disposed in the distal opening of the catheter shaft during delivery of a fluid through the lumen of the catheter shaft.

Alternatively or additionally to any of the examples above, in another example, the coiled portion may have a third flexibility less than the first flexibility and greater than the second flexibility.

Alternatively or additionally to any of the examples above, in another example, the plurality of apertures may be formed in a radially outward sidewall of the coiled portion.

Alternatively or additionally to any of the examples above, in another example, when the coiled portion is disposed over the proximal end region of the guidewire, the guidewire may bias the coiled portion from the preformed coiled configuration into a straight configuration.

Alternatively or additionally to any of the examples above, in another example, when the coiled portion is disposed over the distal end region of the guidewire, the tubular member may bias the guidewire into a helical configuration.

Alternatively or additionally to any of the examples above, in another example, the infusion catheter system may further comprise a fluid delivery device fluidly coupled to the proximal end region of the catheter shaft.

Alternatively or additionally to any of the examples above, in another example, the fluid delivery device may comprise a syringe.

Alternatively or additionally to any of the examples above, in another example, the fluid delivery device may comprise an infusion pump.

Alternatively or additionally to any of the examples above, in another example, the fluid delivery device may be configured to deliver a therapeutic drug to the lumen of the catheter shaft.

Alternatively or additionally to any of the examples above, in another example, the coiled portion may be configured to be biased into a straight configuration during delivery of the coiled portion to a treatment location and may be configured to recoil towards the preformed coiled configuration when positioned adjacent to the treatment location and a treatment is delivered.

Alternatively or additionally to any of the examples above, in another example, the treatment location may be adjacent to a clot and the treatment is delivery of a lytic.

Alternatively or additionally to any of the examples above, in another example, delivery of the lytic may reduce a size of the clot and as the size of the clot is reduced, the coiled portion may recoil towards the preformed coiled configuration until the coiled portion returns to the preformed coiled portion.

Alternatively or additionally to any of the examples above, in another example, the plurality of apertures may be configured to maintain contact with the clot while the coiled portion recoils towards the preformed coiled configuration.

In another example, an infusion catheter system may comprise an elongate catheter shaft having a proximal end region, a distal end region, a distal opening, and a lumen extending between the proximal end region and distal opening. The distal end region may include a coiled portion having a preformed coiled configuration including a plurality of helically wound rings. A plurality of apertures may be formed through a sidewall of the coiled portion and in fluid communication with the lumen of the catheter shaft. A guidewire may be configured to be slidably disposed within the lumen of the catheter shaft. The guidewire may include a proximal end region having a first outer diameter, a distal end region having a second outer diameter, the second outer diameter greater than the first outer diameter, and an intermediate region disposed between the proximal end region and the distal end region. The intermediate region may have a first flexibility greater than a second flexibility of the proximal end region.

Alternatively or additionally to any of the examples above, in another example, the coiled portion may be formed at least in part of a shape memory material.

Alternatively or additionally to any of the examples above, in another example, the distal end region of the guidewire may be configured to be disposed in the distal opening of the catheter shaft during delivery of a fluid through the lumen of the catheter shaft.

Alternatively or additionally to any of the examples above, in another example, the coiled portion may have a third flexibility less than the first flexibility and greater than the second flexibility.

Alternatively or additionally to any of the examples above, in another example, the plurality of apertures may be formed in a radially outward sidewall of the coiled portion.

Alternatively or additionally to any of the examples above, in another example, when the coiled portion is disposed over the proximal end region of the guidewire, the guidewire may bias the coiled portion from the preformed coiled configuration into a straight configuration.

Alternatively or additionally to any of the examples above, in another example, when the coiled portion is disposed over the distal end region of the guidewire, the tubular member may bias the guidewire into a helical configuration.

Alternatively or additionally to any of the examples above, in another example, the infusion catheter system may further comprise a fluid delivery device fluidly coupled to the proximal end region of the catheter shaft.

Alternatively or additionally to any of the examples above, in another example, the fluid delivery device may comprise a syringe.

Alternatively or additionally to any of the examples above, in another example, the fluid delivery device may comprise an infusion pump.

Alternatively or additionally to any of the examples above, in another example, the fluid delivery device may be configured to deliver a therapeutic drug to the lumen of the catheter shaft.

In another example, an infusion catheter system may comprise an elongate catheter shaft having a proximal end region, a distal end region, a distal opening, and a lumen extending between the proximal end region and distal opening. The distal end region may include a coiled portion formed at least in part from a shape memory material and having a preformed coiled configuration including a plurality of helically wound rings. A plurality of apertures may be formed through a sidewall of the coiled portion such that the plurality of apertures are oriented in a radially outward direction when the coiled portion is in the preformed coiled configuration. The plurality of apertures may be in fluid communication with the lumen of the catheter shaft. A fluid delivery device may be fluidly coupled to the proximal end region of the catheter shaft. A guidewire may be configured to be slidably disposed within the lumen of the catheter shaft. The guidewire may include a proximal end region having a first outer diameter, a distal end region having a second outer diameter, the second outer diameter greater than the first outer diameter, and an intermediate region disposed between the proximal end region and the distal end region. The intermediate region may have a first flexibility greater than a second flexibility of the proximal end region.

Alternatively or additionally to any of the examples above, in another example, the distal end region of the guidewire may be configured to be disposed in the distal opening of the catheter shaft during delivery of a fluid through the lumen of the catheter shaft.

Alternatively or additionally to any of the examples above, in another example, the coiled portion may be configured to be biased into a straight configuration during delivery of the coiled portion to a treatment location and configured to recoil towards the preformed coiled configuration when placed adjacent to the treatment location and a treatment is delivered.

Alternatively or additionally to any of the examples above, in another example, the plurality of apertures may be configured maintain contact with the treatment location while the coiled portion recoils towards the preformed coiled configuration.

An example method of reducing a size of a thrombus in a vessel may comprise advancing a guidewire through a patient's vasculature to a first location. The guidewire may comprise a proximal end region, an intermediate region, and a distal end region. The method may further comprise advancing an infusion catheter over the guidewire. The infusion catheter may comprises an elongate catheter shaft having a proximal end region, a distal end region, a distal opening, and a lumen extending between the proximal end region and distal opening. The distal end region may include a coiled portion having a preformed coiled configuration including a plurality of helically wound rings and a plurality of apertures formed through a sidewall of the coiled portion and in fluid communication with the lumen of the catheter shaft. The method may further comprise retracting the guidewire through the patient's vasculature to a second location proximal to the first location and adjacent to the thrombus. Retracting the guidewire to the second location may bring the plurality of apertures into contact with the thrombus. The method may further comprise positioning the distal end region of the guidewire in the distal opening of the catheter shaft and administering a therapeutic drug through the lumen of the catheter shaft. The position of the distal end region of the guidewire may direct the therapeutic drug through the plurality of apertures.

Alternatively or additionally to any of the examples above, in another example, the coiled portion may be configured to be biased into a straight configuration during the step of advancing the infusion catheter over the guidewire and configured to recoil towards the preformed coiled configuration when the guidewire is retracted to the second location.

Alternatively or additionally to any of the examples above, in another example, the therapeutic drug may be a lytic.

Alternatively or additionally to any of the examples above, in another example, administering a therapeutic drug may reduce a size of the thrombus and as the size of the thrombus is reduced, the coiled portion may recoil towards the preformed coiled configuration until the coiled portion returns to the preformed coiled portion.

Alternatively or additionally to any of the examples above, in another example, the plurality of apertures may be configured to maintain contact with the thrombus while the coiled portion recoils towards the preformed coiled configuration.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Thrombectomy catheters and systems may be used to remove thrombus, plaques, lesions, clots, etc. from veins or arteries. These devices may be effective to remove acute thrombus but may be less effective on older or more organized thrombus, or areas of large clot burden such as that seen in deep vein thrombosis (DVT). It may be desirable to provide an infusion system that can keep the lytics in direct contact (or as close as possible) with the clot as the clot is dissolved.

Figure 1:
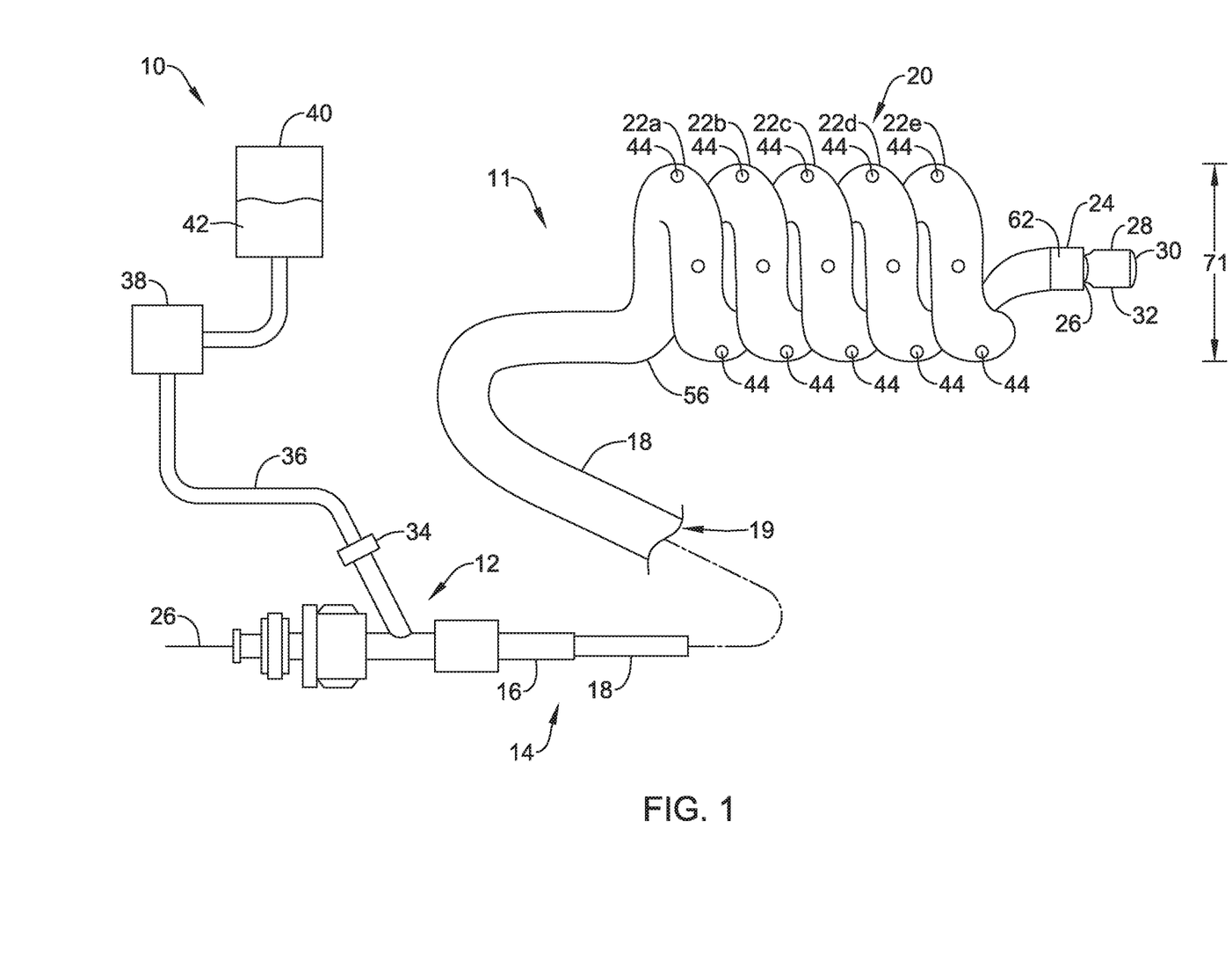
FIG. 1 is a schematic view of an illustrative low pressure infusion catheter system in a first configuration.

FIG. 1 is a schematic view of an illustrative low pressure infusion catheter system 10 in a first configuration. The infusion catheter system 10 may be configured to deliver a fluid (e.g. a thrombolytic drug or therapeutic agent) through a plurality of holes or apertures 44 to a vessel. In one example, the thrombolytic drugs delivered to the vessel include, but are not limited to, lytics (e.g., tissue plasminogen activator (tPA)) or other drugs that interact with a thrombus and actively reduce the size (e.g. breakdown, dislodge, minimize or eliminate) the thrombus. In some examples, after the catheter system 10 delivers the lytics or other drugs to actively reduce the size of the thrombus, a thrombectomy catheter may be used to further macerate and aspirate any remaining thrombus within the vessel. For example, once catheter system 10 has treated the thrombus with the lytics or other drugs, the thrombectomy catheter is used to clear any remaining thrombus. In an example, using the catheter system 10 in combination with a thrombectomy catheter can reduce the overall procedure time. Examples of thrombectomy catheters are described in Bonnette et al., U.S. Patent Publication No. 2006/0129091, entitled "ENHANCED CROSS STREAM MECHANICAL THROMBECTOMY CATHETER WITH BACKLOADING MANIFOLD," Bonnette et al., U.S. Pat. No. 6,676,637, entitled "SINGLE OPERATOR EXCHANGE FLUID JET THROMBECTOMY METHOD," and Bonnette et al., U.S. Pat. No. 6,945,951, entitled "THROMBECTOMY CATHETER AND SYSTEM," which are hereby incorporated herein by reference in their entirety.

The illustrative infusion catheter system 10 may include a catheter 11 and a manifold assembly 12. The catheter 11 may include an elongate catheter shaft 18 extending from a proximal end region 14 to a distal end region 24. A lumen 19 may extend from the proximal end region 14 to the distal end region 24 of the catheter shaft 18. The distal end region 24 may include a coiled or helical portion 20 configured to deliver a thrombolytic drug or other fluid to a vessel through the plurality of apertures 44. A strain relief fitting 16 may be coupled to the manifold assembly 12 and the proximal end region 14 of the catheter shaft 18. In some embodiments, the proximal end region 14 may extend through a lumen of strain relief fitting 16.

A fluid delivery device 38 may be coupled through a tube 36, or other means (e.g. a needle), to manifold assembly 12 at a side port 34 of the manifold assembly 12. The side port 34 may be in fluid communication with the lumen 19 of the catheter shaft 18 such that the fluid delivery device 38 is fluidly coupled to the catheter shaft to deliver fluid 42 through the apertures 44 in the coiled portion 20 and to a vessel. In some embodiments, the fluid delivery device 38 may be a drug infusion pump or injector. In other embodiments, the fluid delivery device 38 may be syringe. The fluid delivery device 38 may pump a volume of a fluid 42 from a fluid reservoir 40, if so provided, into the lumen 19 to generate a pressurized source of fluid within the lumen 19. In an example, the fluid 42 may include thrombolytic drugs such as lytics, and the pressurized source of fluid generates fluid jets when directed through the one or more apertures 44 of the coiled portion 20. In some instances, the fluid 42 may be provided at pressures of 600 pounds per square inch (psi) (4136 kilopascals (kPa)) or less, 500 psi (3447 kPa) or less, 400 psi (2758 kPa) or less, 250 psi (1724 kPa) or less, 100 psi (689 kPa) or less, as desired. In an example, the one or more apertures 44 provide corresponding fluid jets at flow rates low enough to not cause appreciable hemolysis. Some example fluid delivery devices 38 are described in Cowan et al., U.S. Pat. No. 7,666,169, entitled "SYRINGE AND SYRINGE PLUNGERS FOR USE WITH MEDICAL INJECTORS" and Critchlow et al., U.S. Pat. No. 6,520,930, entitled "INJECTORS, INJECTOR SYSTEMS AND INJECTOR CONTROL", which are hereby incorporated herein by reference in their entirety. In some embodiments, a controller may be provided to allow for the automation and/or metering of the fluid delivery process.

The coiled portion 20 of the catheter shaft 18 may generally take the form of a helix including a plurality of windings or rings 22a, 22b, 22c, 22d, 22e (collectively 22). The size and spacing of the rings 22 may be varied, as described herein. In some embodiments, the coiled portion 20 may comprise a polymeric tubular element attached (e.g. weld, melt, bond, etc.) to a distal portion of the catheter shaft 18. Alternatively, coiled portion 20 may be formed as a unitary structure with the catheter shaft 18. In other embodiments, the coiled portion 20 may be formed from a composite tubular element attached (e.g. weld, melt, bond, etc.) to the distal portion of the catheter shaft 18.

Some medical devices may be designed to have particular physical characteristics such as flexibility (e.g., for the purposes of this disclosure, flexibility may be also be termed or expressed as bending stiffness or flexural rigidity). For example, some medical devices may be designed to be very stiff in order to provide enough columnar strength to navigate anatomical areas of resistance. Alternatively, some medical devices may be designed flexible enough in order to bend in a manner sufficient to traverse tortuous anatomy. Therefore, at the distal end of the medical device, it may be desirable to tailor the flexibility of the medical device so that the device can effectively reach its target within the vasculature. It is contemplated that the catheter shaft 18 may be formed to have the desired to flexibility and/or stiffness to navigate the catheter shaft 18 to the desired treatment location.

The catheter shaft 18 may be formed in whole, or in part, from one or more polymeric materials. In some instances, the catheter shaft 18 may include an embedded reinforcement member, such as, but not limited to, a braid member or coil member. The reinforcement member may be formed from a polymer, metal, or composite material, as desired. Some illustrative materials may include stainless steel or nitinol. It is contemplated that the coiled portion 20 may be formed in whole or in part from a shape memory material. The coiled portion 20 may be formed such that the helical shape is the "remembered" or preformed shape. A biasing force (such as a guidewire 26) may bias the coiled portion 20 from its remembered shape to a more linear, or straightened configuration. Once the biasing force is removed, the coiled portion 20 may return to its remembered shape. In other embodiments, electroactive polymers may be used to form the coiled portion 20. The coiled portion 20 may then be transformed between configurations (e.g. coiled and substantially straight) when stimulated by an electric field.

The coiled portion 20 may generally take the form of a helix having a plurality of windings or connected rings 22. In some embodiments, the coiled portion 20 may be formed by winding or wrapping a distal portion of the catheter shaft 18 around a mandrel and set in its "remembered" coiled shape. While the coiled portion 20 is illustrated as including approximately five rings 22, it is contemplated that the coiled portion 20 may include any number of rings desired, such as, but not limited to, less than one, one, two, three, four, or more. A radiopaque marker 62 may be positioned adjacent to the distal end region 24 of the catheter shaft 18. Additionally or alternatively, one or more radiopaque markers may be positioned at any point along the length of the coiled portion 20 and/or the catheter shaft 18 as desired.

The catheter 11 may transition from the generally straight catheter shaft 18 to the helically wound coiled portion 20 at a transition zone or entry point 56 positioned adjacent to the proximal-most ring 22. It is contemplated that the entry point 56 may be along a center line of the coiled portion 20. In other embodiments, the entry point 56 may be at the outer diameter of the rings 22, as shown in FIG. 1, or at point between the center line of the coiled portion 20 and the outer diameter of the rings 22. In yet other embodiments, the entry point 56 may be a point outside of the coiled portion 20.

While the rings 22 are illustrated as having substantially the same outer diameter 71, the outer diameter of the rings 22 may be varied, as desired. For example, the most proximal or most distal ring may have a larger outer diameter than then intermediate rings. This is just an example. The rings 22 may have any combination of outer diameters 71 desired. It is further contemplated that the pitch or the distance between one complete winding or ring, may vary or be the same between adjacent rings 22. A small pitch may result in a coiled portion 20 where the rings 22 are close to an adjacent ring 22 while a large pitch may result in a coiled portion 20 where the rings 22 are positioned further apart from adjacent rings 22.

In some embodiments, the apertures 44 may be formed in the coiled portion 20 after the coiled portion 20 has been formed. This may allow most or all of the apertures 44 to be formed in region of the coiled portion 20 that would face a vessel wall when the catheter shaft 18 is disposed within a vessel. In other words, the apertures 44 may be formed in a radially outward sidewall of the coiled portion 20 and/or oriented in a radially outward configuration. However, this is not required. The apertures 44 may be formed at any time during the manufacturing process or at any position (e.g. an inner surface of the coiled portion 20, an outer surface of the coiled portion 20, between adjacent rings 22, etc.) along the coiled portion 20. The coiled portion 20 may include any number of apertures 44 desired, such as, but not limited to one or more, five or more, 10 or more, 20 or more, 50 or more, etc. In some embodiments, the apertures 44 may be formed at even intervals (e.g. evenly spaced) while in other embodiments, the apertures 44 may be positioned at irregular intervals. In yet other embodiments, the apertures 44 may be positioned in groups or clusters. The one or more apertures 44 may have a circular shape. In an example, the one or more apertures 44 can have a number of different shapes. For example, the one or more apertures 44 include, but are not limited to, circular, ovular, square, triangular, trapezoidal, polygonal, parallelogram, rhomboidal, and other irregular shapes, or combinations thereof. While not explicitly shown, slits or flaps may be added to some or all of the apertures 44 to further control the flow of fluid 42. The apertures 44 may have a diameter in the range of 0.005-0.015 inches (0.127-0.381 mm), in the range of 0.007-0.013 inches (0.178-0.330 mm), or about 0.010 inches (0.254 mm).

Figure 2:
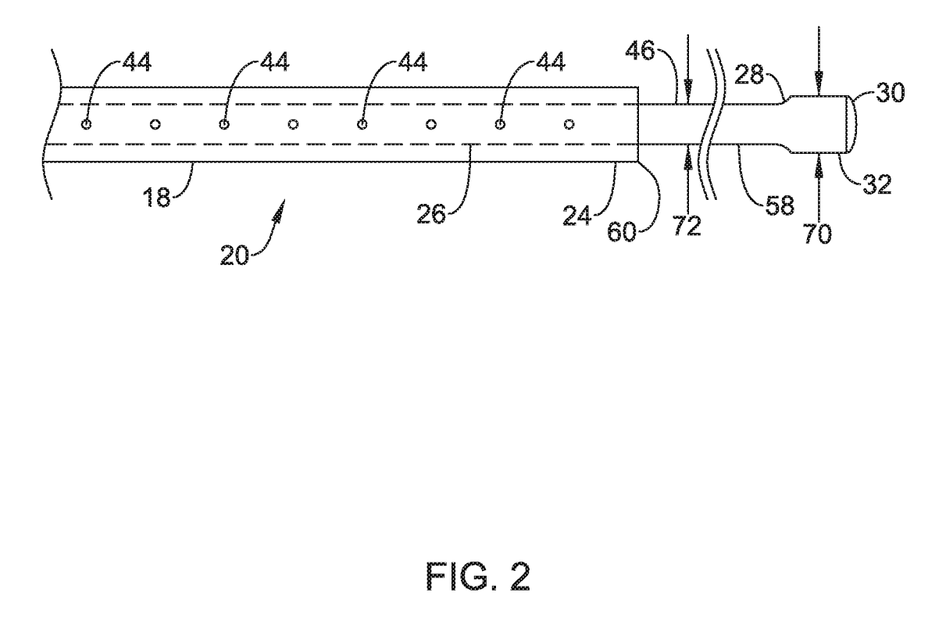
FIG. 2 is a side view of a distal portion of the illustrative catheter system of FIG. 1 in a second configuration.

In some embodiments, the guidewire 26 may include regions of varying flexibility. For example, as shown in FIG. 2, a proximal end region 46 of the guidewire 26 may be stiffer than (or less flexible than) an intermediate region 58 of the guidewire 26 and/or a distal end region 32 of the guidewire 26. The proximal end region 46 may have a first stiffness that is greater than a second stiffness of the intermediate region 58 and/or the distal end region 32. In other words, the intermediate region 58 and/or the distal end region 32 may have a first flexibility that is greater than a second flexibility of the proximal end region 46. These are just examples. The guidewire 26 may include any number of regions each have differing flexibility. Alternatively, or additionally, the guidewire 26 may have a constantly changing flexibility along a length thereof.

Referring to FIG. 2, which illustrates a portion of the coiled portion 20 of FIG. 1 over a guidewire 26, the coiled portion 20 may be formed from a polymeric material having a third flexibility that is greater than the second flexibility of the proximal end region 46 and less than the first flexibility of the intermediate region 58 and/or the distal end region 32. As the stiffness of the proximal end region 46 of the guidewire 26 is greater than the stiffness of the coiled portion 20, the proximal end region 46 of the guidewire 26 may bias, hold, or otherwise deform the coiled portion 20 from the preformed helical shape to a generally straight configuration, as shown in FIG. 2. As the coiled portion 20 is slid or advanced distally along the guidewire 26, the coiled portion 20 approaches the intermediate region 26. As the coiled portion 20 may be stiffer than the intermediate region and/or distal end region 32 of the guidewire 26, the coiled portion 20 may return to its remembered or preformed helical configuration.

For example, a guidewire 26 can be tracked into position and a catheter 11 may be tracked over the guidewire. In other words, the guidewire 26 and the catheter 11 may be slidably disposed relative to one another. As the coiled portion 20 of the catheter shaft 18 is tracked over the stiffer proximal end region 46 of the guidewire 26, the coiled portion 20 of the catheter shaft 18 is straightened to allow for easier advancement of the catheter shaft 18, as shown in FIG. 2. As the coiled portion 20 is tracked over the more flexible intermediate region 58 of the guidewire 26, the coiled portion 20 overcomes the bias of the guidewire 26 and returns to its generally helical shape, as shown in FIG. 1, while also biasing the guidewire 26 into a helical configuration.

In some embodiments, the guidewire 26 may be provided with an enlarged distal end region 32 having an atraumatic distal tip 30. The enlarged distal end region 32 may be sized to have an outer diameter 70 similar in size to an inner diameter of the catheter shaft 18. In some embodiments, the enlarged distal end region 32 may be smaller than the inner diameter of the catheter shaft 18, substantially the same size as the inner diameter of the catheter shaft 18, or larger than the inner diameter of the catheter shaft 18, as desired. It is contemplated that the size and/or position of the enlarged distal end region 32 may be adjusted to adjust the flow rate of the fluid 42 exiting the apertures 44. When fluid 42 is introduced into the lumen 19 of the catheter shaft 18, the guidewire 26 may be positioned such that the enlarged distal region is positioned within or just outside of the distal opening 60 of the catheter shaft 18. This may direct the fluid 42 towards and through the apertures 44 instead of the distal opening 60. It is contemplated that when fluid 42 is provided at a constant pressure and a larger surface area of the distal opening 60 is blocked, the fluid 42 will exit the apertures 44 at a higher flow rate than when a smaller surface area of distal opening 60 is blocked. It is contemplated that some fluid 42 may exit through the distal opening 60.

In some embodiments, the catheter shaft 18 may have an inner diameter in the range of 0.035-0.045 inches (0.889-1.143 millimeters (mm)), or about 0.040 inches (1.016 mm). The enlarged distal end region 32 of the guidewire 26 may have an outer diameter in the range of 0.033-0.043 inches (0.838-1.092 mm), or about 0.038 inches (0.965 mm) while the portion of the guidewire 26 proximal to the enlarged distal end region 32 may have an outer diameter in the range of 0.021-0.031 inches (0.533-0.787 mm), or about 0.026 inches (0.660 mm). These are just examples. It is contemplated that the catheter shaft 18 may be as small as 4 French (Fr) or as large as 8 Fr, as desired. The guidewire 26 and/or enlarged distal end region 32 may be sized according to the size of the catheter shaft 18. For example, a larger diameter catheter shaft 18 may require a larger enlarged distal end region 32 of the guidewire 26 and a smaller diameter catheter shaft 18 may require a smaller enlarged distal end region 32 of the guidewire 26. The guidewire 26 may transition from a proximal outer diameter 72 to the enlarged distal end region 32 at a transition zone 28. In some instances, the transition zone 28 may be a tapered, or sloped region, while in other instance the transition zone 28 may be an abrupt or step-wise transition. In some instances, a gradual slope that occurs over a longer length (compared to steep slope) may allow for the user to more particularly control the percentage of the distal opening 60 blocked by the guidewire 26. In other words, a gradual slope may allow the user to more particularly control the flow rate of the fluid 42 exiting the apertures 44 by controlling the percentage of the distal opening 60 that is blocked by the guidewire 26. While not explicitly shown, the guidewire 26 may be provided with one or more radiopaque markers at any point along the length of the guidewire 26. In one example, a radiopaque marker may be provided adjacent to a transition in flexibility of the guidewire 26 (e.g. between proximal end region 46 and intermediate region 58). This may allow a clinician to position the more flexible intermediate region 58 adjacent to the clot or lesion to more precisely locate the coiled portion 20 of the catheter 11.

Additionally, or alternatively to the enlarged distal end region 32, the guidewire 26 and or the catheter shaft 18 may be provided with an expandable balloon and/or other plug member configured to control the flow of fluid 42 from the distal opening 60. In some instances, the enlarged distal end region 32, balloon, or other plug member may be used to mechanically control the recoiling of the coiled portion 20. For example, the enlarged distal end region 32, balloon, or other plug member may be used to apply a proximal force on the distal end region 24 of the catheter shaft 18 to cause the coiled portion 20 to recoil.

Figure 3:
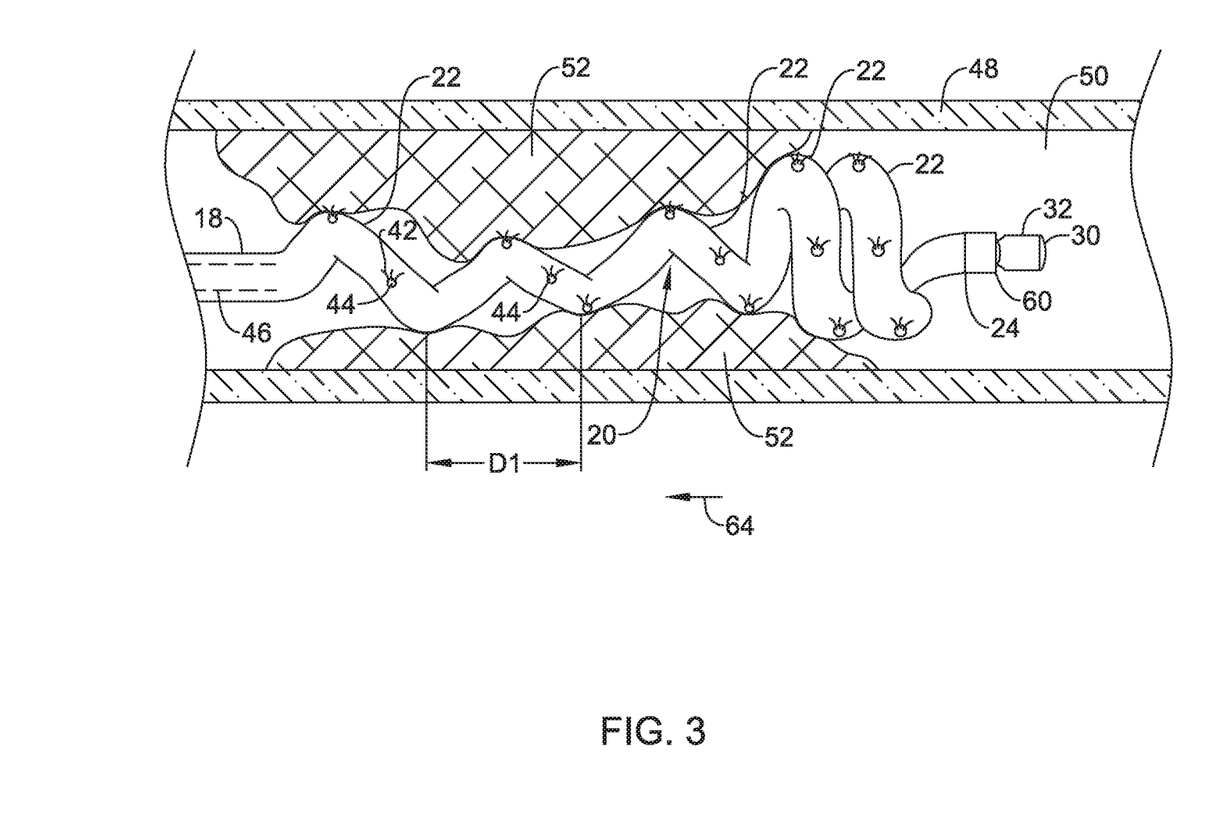
FIGS. 3-5 illustrate a side view of the distal portion of the illustrative catheter system of FIG. 1 in a lumen with a clot, as the clot is dissolved.
Figure 4:
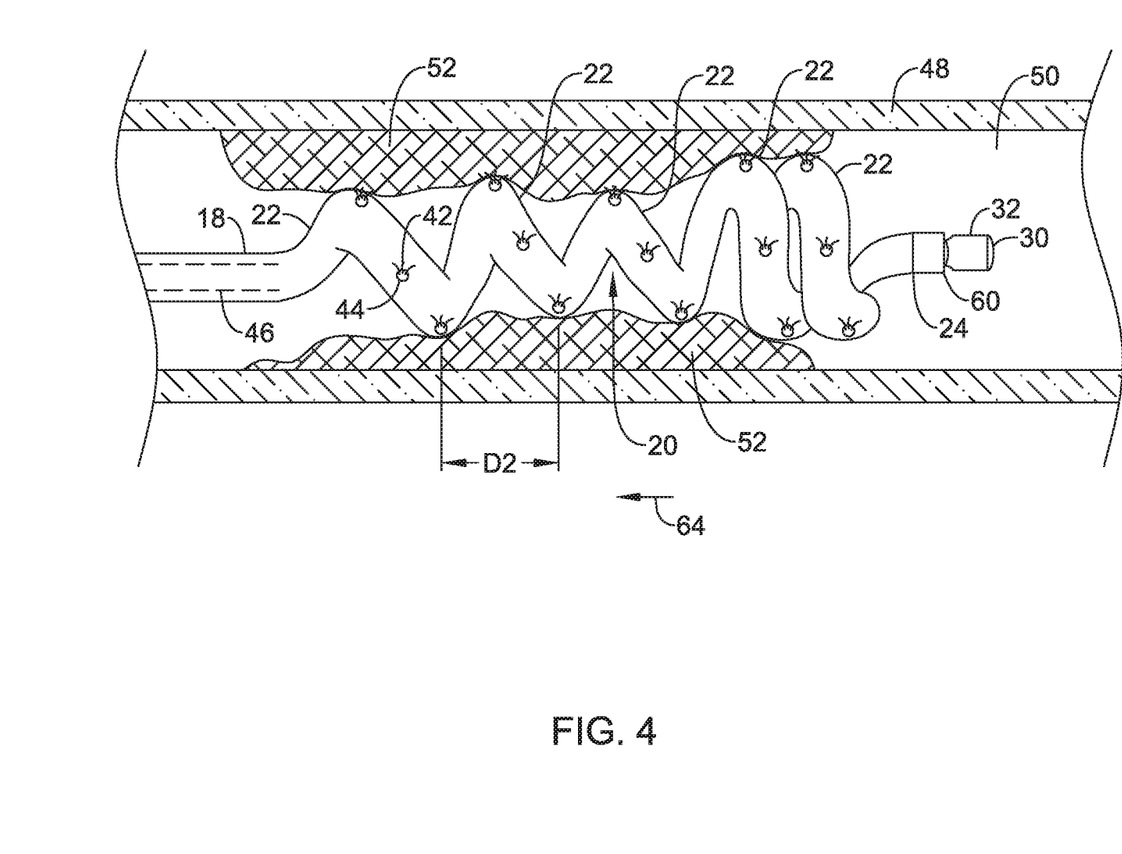

Use of the low pressure infusion catheter system 10 will now be described with respect to FIGS. 3-5 which illustrate the coiled portion 20 positioned in the lumen 50 of a vessel 48 of a patient and adjacent to a lesion, clot, plaque, thrombus, etc. 52. The guidewire 26 may be advanced through the vasculature to a first location such that the distal tip 30 is positioned distal to the clot 52 and/or the intermediate region 58 is positioned adjacent to the clot 52. The catheter 11 may then be advanced over the guidewire 26 towards the clot 52. As described above, the stiff proximal end region 46 of the guidewire 26 may overcome the biasing force of the "remembered" coiled portion 20 such that the coiled portion 20 may be biased into a straight configuration to allow the catheter shaft 18 to be advanced in a substantially straight configuration, as shown in FIG. 2. In some instances, the distal tip 30 of the guidewire may be advanced a sufficient distance past the clot 52 to allow the coiled portion 20 to be positioned adjacent to the clot 52 in a generally straight configuration, although this is not required. Once the coiled portion 20 has been positioned adjacent to the clot 52, the guidewire 26 may be proximally retracted to a second location until the stiff proximal end region 46 is located proximal of the coiled portion 20. For clarity, only a portion of the guidewire 26 that is disposed within the lumen 19 of the catheter shaft 18 has been illustrated in phantom. It should be understood that the guidewire 26 is positioned within coiled portion 20 even when the coiled portion 20 begins to assume its remembered state.

As the guidewire 26 is proximally retracted to the second location, the coiled portion 20 may begin to contract in length along direction 64 while radially expanding (e.g. the coiled portion 20 recoils) bringing the coiled portion 20 and/or the plurality of apertures 44 into contact with the clot. As shown in FIGS. 3 and 4, the clot 52 may block a portion of the vessel lumen 50 such that all or a portion of the coiled portion 20 may not fully return to its remembered state. In such an instance, the coiled portion 20 may contract in length and radially expand until an outer surface contacts the clot 52 thus bringing the coiled portion 20 into intimate contact with the clot 52. In some instances, the clot 52 may be of a size such that the coiled portion 20 cannot appreciably recoil when it is deployed. As can be seen in FIG. 3, the pitch D1 of the rings 22 where the coiled portion 20 cannot fully return to its remembered state may be greater than the pitch D3 of the rings 22 when the coiled portion 20 fully returns to its remembered state (see FIG. 5). Once the coiled portion 20 has been positioned to the user's satisfaction, the guidewire 26 can be proximally retracted to bring the enlarged distal end region 32 into the distal opening 60 of the catheter shaft 18, if it is not already there.

The fluid delivery device 38 may then be used to deliver or administer a flow of fluid 42 through the lumen 19 of the catheter shaft 18. The fluid 42 may exit the catheter shaft 18 through the apertures 44 formed in the sidewall of the coiled portion 20. For example, the position of the distal end region 32 may direct the fluid 42 radially outwards through the plurality of apertures 44. The fluid 42 (e.g., a thrombolytic fluid) may impact and penetrate the clot 52 adjacent to the apertures 44 and actively reduce the size (e.g., break down) and minimize or eliminate the clot 52. In some embodiments, the fluid 42 may weep or drip from the apertures 44 while in other instances, the fluid 42 may spray with more force than a drip. As the clot 52 size is reduced, the coiled portion 20 may continue to contract in length along direction 64 while radially expanding, as shown in FIG. 4. As can be seen in FIG. 4, a pitch D2 of the rings 22 is where the coiled portion 20 has not fully return to its remembered state and, as such, is smaller than the pitch D1 prior to beginning treatment. FIG. 5 illustrates the rings fully returned to an original pitch D3, which, is smaller than pitch D1 and D2. As the clot 52 continues to shrink in size, the coiled portion 20 may continually contract in length along direction 64 while radially expanding. This may help maintain intimate contact between the coiled portion 20 and the clot 52 during delivery of the fluid 42. It is contemplated that the apertures 44 may be positioned such that the apertures 44 maintain contact with (e.g. are directed towards the vessel 48 wall) of the coiled portion 20 as it recoils.

Figure 5:
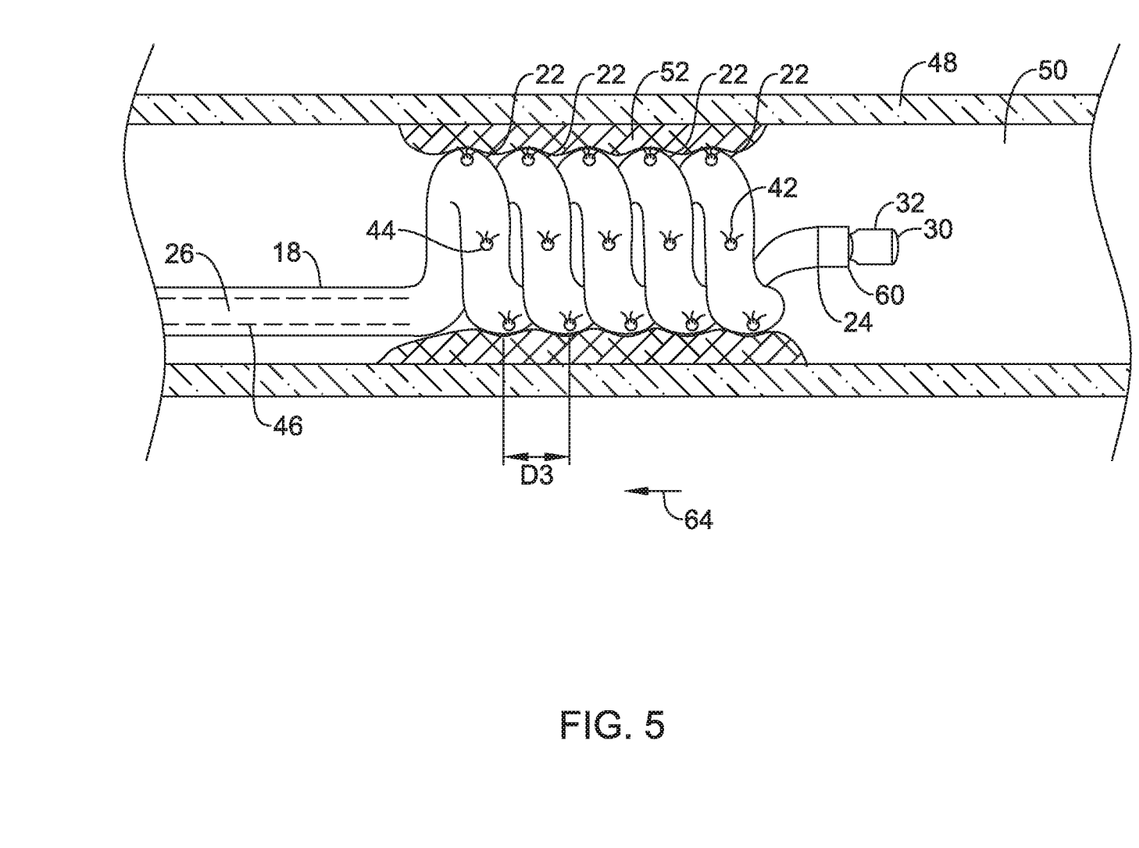

The fluid delivery device 38 may continue to deliver fluid 42 until the clot 52 has been reduced to a desired size, it has been determined that the fluid 42 is no longer reducing the size of the clot 52 and/or the coiled portion 20 has returned to its original "remembered" configured, as shown in FIGS. 1 and 5. To remove the catheter shaft 18 from the vessel 48, the guidewire 26 may be advanced distally until the stiff proximal end region 46 of the guidewire 26 is disposed within the coiled portion 20 and biases the coiled portion 20 to a substantially straight configuration, as shown in FIG. 2, to facilitate removal of the catheter 11. It is contemplated that the guidewire 26 may also be used to straighten the coiled portion 20 to facilitate relocation of the coiled portion 20, if necessary. The catheter shaft 18 may be proximally retracted from the body prior to removing the guidewire 26, or simultaneously with the guidewire 26, as desired. In some embodiments, the guidewire may be left in place to facilitate further treatment with other devices, such as but not limited to a thrombectomy catheter.

The materials that can be used for the various components of the catheter, guidewires, accessory device, and/or other devices disclosed herein may include those commonly associated with medical devices. For simplicity purposes, the following discussion makes reference to accessory devices and their related components. However, this is not intended to limit the devices and methods described herein, as the discussion may be applied to other similar devices, tubular members and/or components of tubular members or devices disclosed herein.

The various components of the devices/systems disclosed herein may include a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In at least some embodiments, portions or all of the accessory devices and their related components may be doped with, made of, or otherwise include a radiopaque material. Radiopaque materials are understood to be materials capable of producing a relatively bright image on a fluoroscopy screen or another imaging technique during a medical procedure. This relatively bright image aids the user of the accessory devices and their related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the accessory devices and their related components to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An infusion catheter system, comprising:
an elongate catheter shaft having a proximal end region, a distal end region, a distal opening, and a lumen extending between the proximal end region and the distal opening, wherein the distal end region includes a coiled portion having a preformed coiled configuration including a plurality of helically wound rings;
a plurality of apertures formed through a sidewall of the coiled portion and in fluid communication with the lumen of the elongate catheter shaft; and
a guidewire configured to be slidably disposed within the lumen of the elongate catheter shaft, the guidewire including a proximal end region having a first outer diameter, a distal end region having a second outer diameter, the second outer diameter greater than the first outer diameter, and an intermediate region disposed between the proximal end region of the guidewire and the distal end region of the guidewire;
wherein the distal end region of the guidewire is configured to be at least partially positioned within the distal opening during delivery of a fluid through the lumen of the elongate catheter shaft and a distal end of the guidewire extends distally beyond a distal end of the elongate catheter shaft; and
wherein when the coiled portion is disposed over the intermediate region of the guidewire, the elongate catheter shaft biases the guidewire into a helical configuration.

2. The infusion catheter system of claim 1, wherein the second outer diameter of the guidewire is approximately the same as an inner diameter of the elongate catheter shaft.

3. The infusion catheter of system claim 1, wherein the second outer diameter of the guidewire is less than an inner diameter of the elongate catheter shaft.

4. The infusion catheter of system claim 1, wherein the distal end region of the guidewire is configured to direct a flow of fluid within the lumen of the elongate catheter shaft towards and through the plurality of apertures.

5. The infusion catheter system of claim 1, wherein the intermediate region of the guidewire has a first flexibility greater than a second flexibility of the proximal end region of the guidewire.

6. The infusion catheter system of claim 5, wherein the coiled portion has a third flexibility less than the first flexibility and greater than the second flexibility.

7. The infusion catheter system of claim 1, wherein the coiled portion is formed at least in part of a shape memory material.

8. The infusion catheter system of claim 1, wherein the plurality of apertures are formed in a radially outward sidewall of the coiled portion.

9. The infusion catheter system of claim 1, wherein when the coiled portion is disposed over the proximal end region of the guidewire, the guidewire biases the coiled portion from the preformed coiled configuration into a straight configuration.

10. The infusion catheter system of claim 1, further comprising a fluid delivery device fluidly coupled to the proximal end region of the elongate catheter shaft.

11. An infusion catheter system, comprising:
an elongate catheter shaft extending along a Z-axis having a proximal end region, a distal end region, a distal opening having an area extending along the X-Y plane, and a lumen extending between the proximal end region and the distal opening, wherein the distal end region includes a coiled portion formed at least in part from a shape memory material and having a preformed coiled configuration including a plurality of helically wound rings;
a plurality of apertures formed through a sidewall of the coiled portion such that the plurality of apertures are oriented in a radially outward direction when the coiled portion is in the preformed coiled configuration, the plurality of apertures in fluid communication with the lumen of the elongate catheter shaft;
a fluid delivery device fluidly coupled to the proximal end region of the elongate catheter shaft; and
a guidewire configured to be slidably disposed within the lumen of the elongate catheter shaft, the guidewire including a proximal end region having a first outer diameter, a distal end region having a second outer diameter, the second outer diameter greater than the first outer diameter, and an intermediate region disposed between the proximal end region of the guidewire and the distal end region of the guidewire;
wherein the distal end region of the guidewire is configured to block a percentage of the area of the distal opening of the elongate catheter shaft; and
wherein the intermediate region of the guidewire has a first flexibility greater than a second flexibility of the proximal end region of the guidewire and the coiled portion has a third flexibility less than the first flexibility and greater than the second flexibility.

12. The infusion catheter system of claim 11, wherein a longitudinal position of the distal end region of the guidewire is movable to vary the percentage of the area of the distal opening of the elongate catheter shaft that is blocked.

13. The infusion catheter system of claim 12, wherein increasing the percentage of the area of the distal opening of the elongate catheter shaft that is blocked is configured to increase a flow rate of a fluid exiting the plurality of apertures.

14. The infusion catheter system of claim 12, wherein decreasing the percentage of the area of the distal opening of the elongate catheter shaft that is blocked is configured to decrease a flow rate of a fluid exiting the plurality of apertures.

15. The infusion catheter system of claim 11, wherein the coiled portion is configured to be biased into a straight configuration during delivery of the coiled portion to a treatment location and configured to recoil towards the preformed coiled configuration when placed adjacent to the treatment location and a treatment is delivered.

16. The infusion catheter system of claim 15, wherein the plurality of apertures are configured to maintain contact with the treatment location while the coiled portion recoils towards the preformed coiled configuration.

17. An infusion catheter system, comprising:
   an elongate catheter shaft having a proximal end region, a distal end region, a distal opening, and a lumen extending between the proximal end region and the distal opening, wherein the distal end region includes a coiled portion formed at least in part from a shape memory material and having a preformed coiled configuration including a plurality of helically wound rings;
   a plurality of apertures formed through a sidewall of the coiled portion such that the plurality of apertures are oriented in a radially outward direction when the coiled portion is in the preformed coiled configuration, the plurality of apertures in fluid communication with the lumen of the elongate catheter shaft;
   a fluid delivery device fluidly coupled to the proximal end region of the elongate catheter shaft; and
   a guidewire configured to be slidably disposed within the lumen of the elongate catheter shaft, the guidewire including a proximal end region having a first outer diameter, a distal end region having a second outer diameter, the second outer diameter greater than the first outer diameter, and an intermediate region disposed between the proximal end region and the distal end region;
   wherein the distal end region of the guidewire is movable relative the distal opening of the elongate catheter shaft to adjust a flow rate of a fluid exiting the distal opening and the plurality of apertures during delivery of the fluid through the lumen of the elongate catheter shaft; and
   wherein when the coiled portion is disposed over the intermediate region of the guidewire, the elongate catheter shaft biases the guidewire into a helical configuration.

* * * * *